United States Patent [19]

Lasner

[11] Patent Number: 5,120,171
[45] Date of Patent: Jun. 9, 1992

[54] BONE SCREW WITH IMPROVED THREADS

[75] Inventor: Jeffrey Lasner, Purchase, N.Y.

[73] Assignee: Stuart Surgical, Greensburg, Pa.

[21] Appl. No.: 618,500

[22] Filed: Nov. 27, 1990

[51] Int. Cl.⁵ .............................................. F16B 39/30
[52] U.S. Cl. ................................... 411/308; 411/310; 411/426; 606/73
[58] Field of Search ............... 411/306, 307, 308, 309, 411/310, 311, 415, 411, 424, 426, 414, 453; 606/65, 72, 73, 86

[56] References Cited

U.S. PATENT DOCUMENTS

| | | |
|---|---|---|
| Re. 28,111 | 1/1971 | Laverty . |
| D. 51,291 | 9/1917 | Vorel . |
| D. 52,511 | 1/1918 | Groh . |
| 197,933 | 12/1877 | Harvey . |
| 1,891,895 | 12/1932 | Nagel ................................ 411/453 |
| 1,980,093 | 11/1934 | Rosenberg . |
| 2,005,672 | 6/1935 | Chaffee ............................. 411/414 |
| 2,570,465 | 10/1951 | Lundholm .......................... 128/92 |
| 2,696,817 | 12/1954 | Prevo ................................. 128/92 |
| 2,702,543 | 2/1955 | Pugh et al. ......................... 128/92 |
| 2,772,676 | 12/1956 | Pohl ................................... 128/92 |
| 3,109,691 | 11/1963 | Burkhardt ........................ 339/100 |
| 3,233,500 | 2/1966 | de Vellier . |
| 3,466,748 | 9/1969 | Christensen ........................ 606/73 |
| 3,492,906 | 2/1970 | Hauser ............................... 411/415 |
| 3,703,843 | 11/1972 | Laverty . |
| 3,861,269 | 1/1975 | Laverty . |
| 4,175,555 | 11/1979 | Herbert ............................. 411/415 |
| 4,177,524 | 12/1979 | Grell et al. .......................... 3/1.9 |
| 4,261,351 | 4/1981 | Scherfel ........................ 128/92 BC |
| 4,463,753 | 8/1984 | Gustilo ........................... 128/92 B |
| 4,569,338 | 2/1986 | Edwards ............................. 606/73 |
| 4,640,271 | 2/1987 | Lower ............................ 128/92 YF |
| 4,756,653 | 7/1988 | Berger ............................... 411/426 |
| 4,791,918 | 12/1988 | Von Hasselbach ............. 128/924 K |
| 4,870,957 | 10/1989 | Goble et al. ................... 128/92 YF |

FOREIGN PATENT DOCUMENTS

| | | | |
|---|---|---|---|
| 77837 | 6/1918 | Switzerland ........................ 411/415 |
| 2033755 | 5/1980 | United Kingdom . |
| 2090745 | 7/1982 | United Kingdom . |

OTHER PUBLICATIONS

"Youngstown Sliding Lag Screw and Plate" News Release dated Sep. 1, 1988.

"Dr. Virgin Hip Fixation Screw", *Surgical Equipment*, vol. 7, No. 4, pp. 14 and 15, Jul., 1940.

*Primary Examiner*—Neill R. Wilson
*Attorney, Agent, or Firm*—Nixon & Vanderhye

[57] ABSTRACT

A bone screw having a helical thread that gradually increases in thickness from the tip to the head of the screw. The thin thread at the tip of the screw can be inserted into a bone with minimal tearing or cracking of the bone. The thicker treads ascending form the tip to the head of the screw displaces bone against the superior (top) thread surfaces. This displacement of bone increases the screw's resistance to being pulled-out of the bone. The thicker core just below the screw head increases the screw's ability to withstand compressive and distractive loads. The core is thickest just below the head because it is at that point on the screw that the fulcrum loads are greatest.

9 Claims, 2 Drawing Sheets

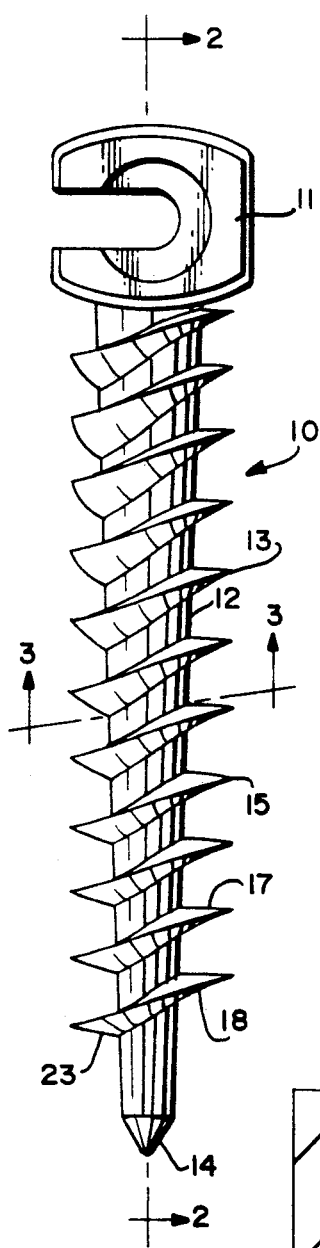
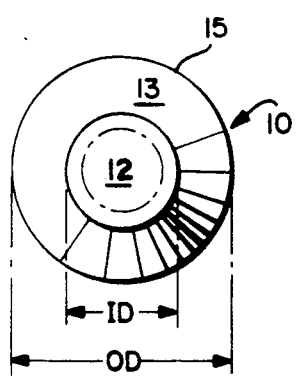
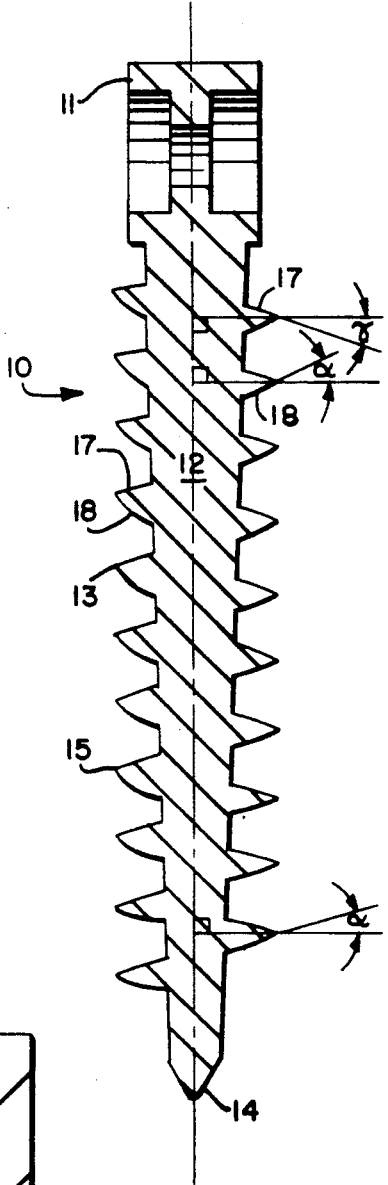
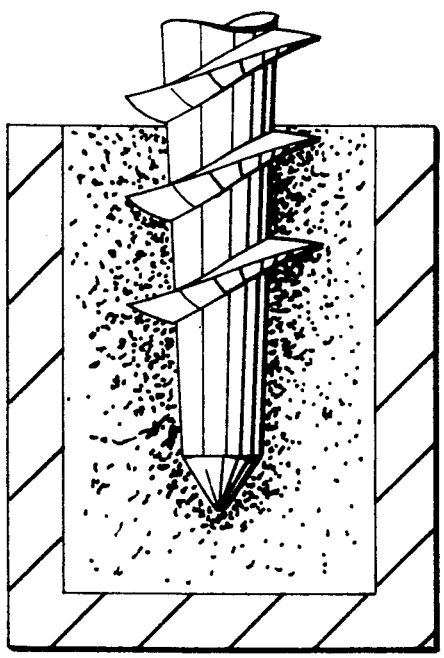

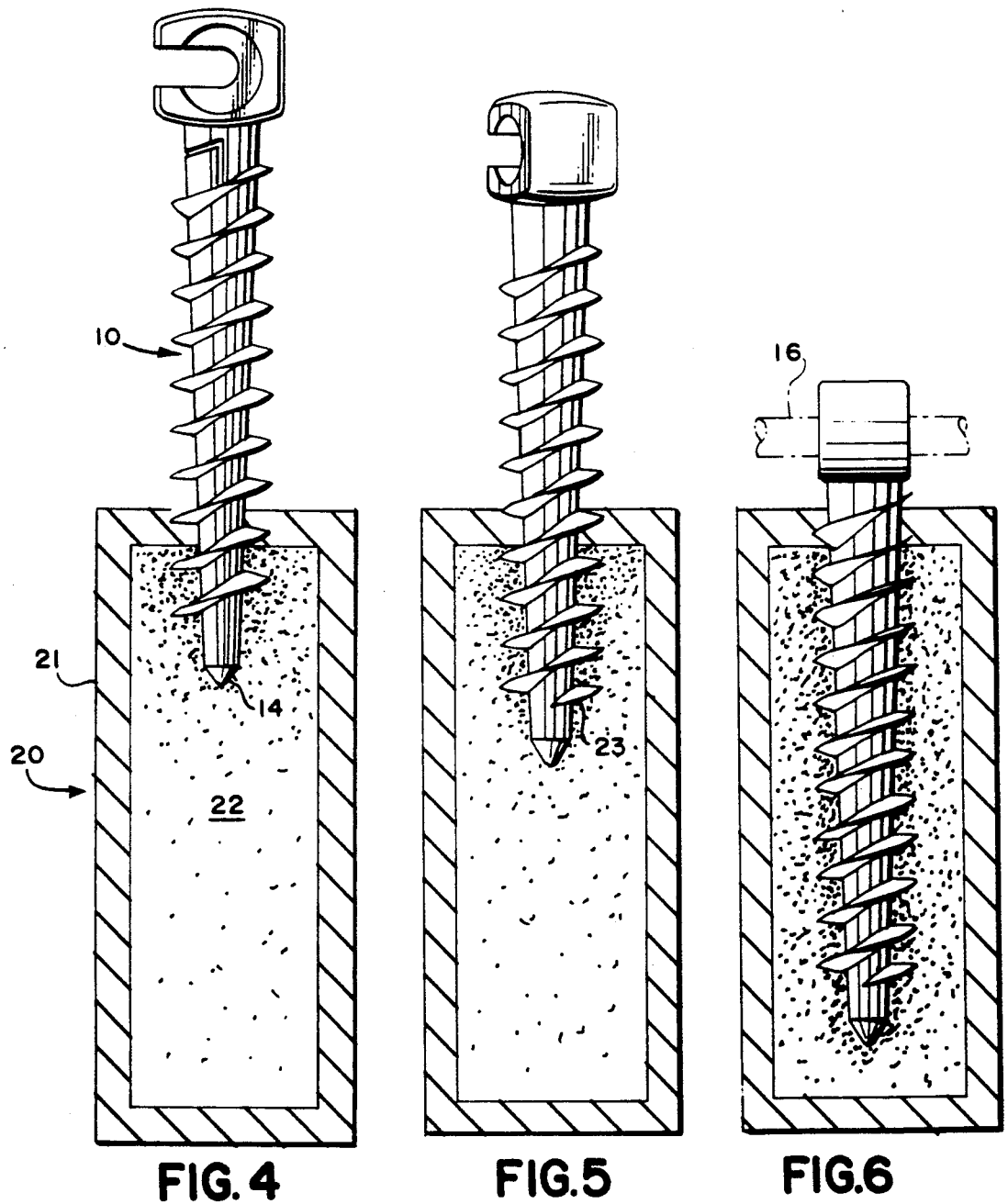
FIG. 4  FIG. 5  FIG. 6

BONE SCREW WITH IMPROVED THREADS

FIELD OF THE INVENTION

This invention relates to a screw having helical threads that become thicker from the tip to the head of the screw. The screw can be used in bones, soft woods, laminated partial boards and other similar materials.

BACKGROUND AND SUMMARY OF THE INVENTION

Although bone screws are known, the threads on bone screws have been given scant attention. The threads anchor the screw into the bone. The treads keep the screw from being axially pulled out of the bone. The threads cut a helical path into the bone as the screw rotates into the bone. Given the importance of the screw threads, it is surprising that there was no reference known to me on the design of screw thread shapes.

There are many variable aspects of thread shape. The thread can have a sharp or blunt apex. The pitch of the thread can be varied. A shallow thread pitch provides many turns around the screw with each turn close to adjacent turns. A steep pitch provides few turns with the turns spaced far apart. The height of the thread from the surface of the screw core to the apex of the thread can be deep or shallow. The thickness of the thread can be varied.

Threads have a superior surface on the side facing the screw head and an inferior surface facing the screw tip. The engagement of the superior surface with the bone provides resistance to screw pull-out. The angle between the inferior and superior surfaces is the thread angle. If this angle is small, the thread is narrow as is a knife. If the thread angle is large, then the thread is wide and strong. The need for a knife-like thread to cut through the bone must be balanced against the need for a strong thread.

There are a few references regarding thread shape. U.S. Pat. No. 4,463,753, issued Aug. 7, 1984, entitled "Compression Bone Screw" discloses that the angle made by a thread cross-section is "critical" to the operation of the screw. The angle between the superior and inferior thread surface should be between 30 and 50 degrees, with 40 degrees being optimal according to the '753 Patent. Threads having an angle of less than 20 degrees are weak and can fail. If the angle is greater than 60 degrees, the tread will strip out the bone between the treads. Similarly, U.S. Pat. No. 4,870,957, issued Oct. 3, 1989, and entitled "Ligament Anchor System" discloses a range of angles for the inferior and superior surfaces of the threaded studs that it discloses.

I have found that bone screws can be improved by varying the cross-sectional shape of the thread from the tip to the head of a screw. The thickness of the thread near the tip of the screw has a narrow cross-section. The narrow thread easily cuts into the bone as the screw rotates into the bone. There is minimal tearing and displacement of the bone by the insertion of the narrow thread. The thread becomes thicker toward the head of the screw to increase thread strength and to displace bone matter downward against the superior thread surface.

The cross-section of the thread gradually thickens from the tip to the head of the screw. It is preferable that the thread be thickened by increasing the angle between the inferior thread surface and a line normal to the screw axis. This angle is smallest at the screw tip and widest at the head. The angle of the superior surface is constant along the length of the screw. By thickening the thread, the inferior surface shifts downward toward the adjacent superior surface. Accordingly, as the thread rotates into the bone, the inferior thread surface gradually displaces the bone matter between the threads down against the adjacent superior thread surface.

The bone matter is compressed against the superior thread surface and partially rotated downward against the superior surface. Compressing bone matter against the superior surface increases the bone resistance to thread pull out. Similarly, rotating bone matter downward aligns the bone matter to enhance the resistance to axial load forces on the screw.

By increasing the thread thickness in the direction of the screw head, the thread is thickest and strongest near the head. This is particularly advantageous in bones because of the hard cortical bone shell. The cortical bone is harder and more compact than the spongy cancellous matter in the center of bones. The cortical bone provides the bulk of the bone's resistance to screw pull-out forces (axial load forces). The thread near the screw head engages the cortical bone and, thus, carries much of the axial load on the screw. The thicker threads of the present invention are optimal for supporting large loads at the cortical bone. Moreover, the varying thickness of the thread compresses and rotates the cortical bone downward against the superior screw surface to provide enhanced pull-out resistance. Also, the thicker core at the head enhances the lateral load to failure strength of the screw. The core is thickest near the head which is where the greatest lateral compression and distractive forces act on the screw. These forces act to bend the screw just below the head and the thick core near the head provides the greatest resistance to bending.

It is an object of my invention to provide an improved screw for bones, laminated woods, and other materials. In particular, it is an object of my invention to enhance the pull out resistance of screws for bones and other materials. In addition, it is an object of my invention to provide a screw able to withstand large load forces without shearing off the head of the screw or pulling the screw out of its position.

BRIEF DESCRIPTION OF THE DRAWINGS

FIG. 1 is a side view of a preferred embodiment of my screw invention;

FIG. 2 is a longitudinal cross-sectional view along line 2—2 of FIG. 1;

FIG. 3 is an axial cross-section along line 3-3 of FIG. 1;

FIG. 4 to 6 are side views showing a preferred embodiment of my screw invention being threaded into a bone; and FIG. 7 is an enlarged side view of a screw tip in a bone.

DETAILED DESCRIPTION OF THE DRAWINGS

FIGS. 1 to 3 show the preferred embodiment of the bone screw 10. The screw has a head 11 attached to a core 12 that has a helical screw thread 13. The core is a tapered cylindrical shaft. The core can be solid for enhanced strength or have an axial channel to allow medical devices, e.g., stylet or optical fibers, to pass through the screw into the bone. The core has a pointed tip 14 at its end opposite to the head. The diameter of the core is smallest at the tip. The diameter gradually increases along the length of the core and the largest diameter is adjacent the screw head.

The diameter of the core is the inside diameter (ID) of the screw. The outside diameter (OD) of the screw is the distance from thread apex 15 through the screw axis to thread apex. In the preferred embodiment, the outside diameter is constant along the length of the screw. However, the OD may be varied in other embodiments.

The depth of the screw thread is the distance between the thread apex 15 and the outer surface of the core. The thread depth is one-half the difference between the outside and inside diameters of the thread. In the preferred embodiment, the thread depth is greatest near the tip 14 and decreases along the length of the screw toward the head 11.

The thread forms a helical spiral around the core. In the preferred embodiment there is only one thread. Other embodiments may have more than one threads circling the core. The number of threads and thread pitch are parameters that persons of ordinary skill in screw design routinely select. Moreover, these parameters depend on the type of bone or other material that the screw is to be inserted and on the purpose of the screw. If the screw is to anchor a rod 16 (FIG. 6) to support the spine, then the thread pitch and other screw parameters should be selected so that the screw can withstand large shearing and axial loads. If the screw is to be used for other purposes, then other factors will dictate the selection of screw design parameters.

The tread has a superior surface 17 and an inferior surface 18. The superior surface faces the screw head and the inferior surface faces the tip. Both surfaces form a narrow ribbon helix around the core. Both surfaces are continuous along the length of the core. The apex 15 of the screw thread is the ridge formed by the intersection of the superior and inferior surfaces of the thread. In the preferred embodiment, the apex is sharp to cut through the bone.

The superior surface forms an angle gamma ($\gamma$) with a line normal to the axis of the screw. Angle gamma is constant for the entire screw. The superior surface maintains a constant orientation with respect to the axis of the screw.

The inferior surface 18 forms angle alpha ($\alpha$) with a line normal to the screw axis. Angle alpha is small near the tip and large near the screw head. As the inferior surface curls around the core from the tip to the head, angle alpha gradually expands the thickness of the thread. In the preferred embodiment, angle alpha increases linearly. It is contemplated that angle alpha can increase at any suitable rate in other embodiments of the invention.

The screw of this invention can be made using ordinary and well-known screw manufacturing techniques. Persons of ordinary skill in bone screw manufacture are able to make a screw as described in this application with at most ordinary and routine experimentation. I am not aware of any optimal or best method to be used to manufacture the screw. The screw can be made of the same bio-compatible materials used to make prior bone screws. I have not found that any one screw material is best suited for my invention.

FIGS. 4 to 7 shown the bone screw 10 being inserted into a bone 20 and in operation. The bone has a hard cortical shell 21 and covering a loose, porous cancellous bone 22. The cortical shell is relatively strong but somewhat brittle. The cortical bone is easily cracked and broken by bone screws. However, the shell provides a substantial portion of the resistance force to the bone screw. The spongy cancellous bone provides some resistance to the screw but can be easily torn.

A pilot hole, with stylet (not shown), is sometimes made by the surgeon in the bone before inserting the bone screw. Inserting the stylet before screw placement allows the surgeon to use radiographic imaging techniques to ensure that the subsequent screw placement will not damage the bone or nerves when fully inserted. For example, screws inserted into the pedicle of vertebra could, if misplaced, damage the nerves in the spinal cord. Accordingly, a surgeon must be careful to position the screw where it will provide a firm and secure anchor without harming the patient.

As shown in FIGS. 4 and 7, the cancellous spongy bone 22 is displaced as the tip 14 of the screw passes through the bone. The screw tip is tapered but not sharp to avoid estravication through opposite or laterally positioned cortical bone as when the screw is not aligned properly with the bone. The tapered but blunt tip passes through the cortical bone without cracking or damaging the bone. The displaced cancellous bone 22 is pushed slightly downward by the screw tip but remains adjacent the screw. Moreover, the cancellous material does not tear or rip away from the surface of the core or threads.

The leading edge 23 of the thread (FIG. 5) cuts a path in the bone for the thread. The leading edge of the thread is thin and sharp, similar to a knife edge. The thread is thin near the tip because angle alpha is small so that the inferior surface is nearly normal to screw axis. Since the apex of the thread is knife sharp, it easily cuts through the hard cortical bone without cracking the bone. Similarly, the sharp thread cuts through the soft cancellous bone without tearing or ripping the interior of the bone. Accordingly, the leading edge of the thread creates a narrow passageway through the bone for the thread.

As the screw is rotated downward into the bone, the core thickness increases. The core continually pushes the cancellous matter radially outward and, thus, slightly compresses the cancellous matter surrounding the bone and between the threads. Similarly, as the screw thread moves deeper into the bone, the thickness of the thread in the bone gradually increases. As the angle alpha of the inferior surface of the screw thread expands, the cancellous bone matter immediately below the inferior surface is displaced downward against the lower adjacent superior thread surface. This displacement further compacts the cancellous matter between the threads and against the screw.

By displacing bone downward against the superior surface of the screw thread, the bone's resistance to screw pull-out is increased. The hard cortical shell is gradually turned downward against the superior surface of the screw as the screw rotates into the bone. This downward deflection of the cortical bone places it in a better orientation to oppose axial pull-out forces on the screw.

In addition, the cortical bone is pinched tightly between opposing inferior and superior thread surfaces. As the screw rotates into the bone, the thread thickens and reduces the volume between the threads. The cortical bone is compressed between the threads besides being turned slightly downward. The pinching of the cortical bone between the thread further increases the resistance of the bone to pull-out and to shear loads. Moreover, the thread and core are thickest and, thus, strongest at the cortical bone. Accordingly, the screw is able to withstand high loads at the cortical bone owing to the fact that the force fulcrum is located just below the head where the core is thickest.

The cancellous bone also provides support for the bone screw. By gradually increasing the thickness of the thread, the passageway in the cancellous bone is gradually displaced without tearing away from the threads. The cancellous bone is displaced by the inferior surface of the thread and pushed down against the superior thread surface. This compresses the cancellous bone between the threads and orients the bone to oppose screw pull-out. The compaction and orientation of the bone improve the support provided by the cancellous bone and, thereby, increase the pull-out resistance of the screw.

The invention has been described in what is considered to be the most practical and preferred embodiment. The invention is not limited to the disclosed embodiment and covers various modifications and equivalent structures included within the spirit and scope of the appended claims.

What is claimed is:

1. A fastener comprising a core having a tip and a head, and a thread attached to and curling around said core, the cross-sectional thickness of said thread gradually increasing from the tip to the head of said core, the angle between the inferior surface of said thread and said core gradually decreasing from the tip to the head of said core and the volume of the gap between adjacent thread sections on said core decreasing from the tip to the head of said core.

2. A fastener as in claim 1 wherein said core is a cylindrical shaft and said thread is at least one helix that curls around said shaft.

3. A fastener as in claim 1 wherein said thread gradually increases in thickness by varying the orientation of an inferior surface on said thread.

4. A fastener as in claim 1 wherein said cross-sectional thickness of said tread has an inferior side gradually increasing in thickness from the tip to the head of said core.

5. A screw comprising:
a core having a tip at one end and a head at the other end, and
a thread helix attached to said core and curling around the axis of said core, the cross-sectional thickness of said thread increasing in the direction from the tip to the head of said screw, the gap between adjacent thread sections on said core decreasing in the direction from the tip to the head of the screw, and said thread having an inferior surface, the orientation of said inferior surface changing along the length of said core.

6. A screw as in claim 5 wherein said thread having inferior and superior surfaces, the orientation of said inferior surface changing so as to increase the thickness of said thread.

7. A screw as in claim 6 wherein said superior surface has a substantially constant orientation along the length of said core.

8. A screw as in claim 6 or 7 wherein said inferior surface forms an angle with respect to the normal to the screw axis and said angle gradually increases along the direction from the tip to the head of the screw.

9. A screw comprising a core shaft having a screw thread having a substantially constant outer diameter,
the cross-sectional area of said thread gradually increasing as said thread advances along said core in a first direction, the gap between adjacent sections of said thread narrowing as said thread advances along said core in said first direction, and
said thread having an inferior surface forming an angle to said core that decreases as said thread advances along said core in said first direction.

* * * * *